United States Patent [19]

Sabatelli

[11] Patent Number: 4,937,370
[45] Date of Patent: Jun. 26, 1990

[54] NOVEL CHROMOPHORES, SUNSCREEN COMPOSITIONS AND METHODS FOR PREVENTING SUNBURN

[75] Inventor: Anthony D. Sabatelli, Hamilton, Ohio

[73] Assignee: The Procter & Gamble Company, Cincinnati, Ohio

[21] Appl. No.: 54,085

[22] Filed: Jun. 2, 1987

[51] Int. Cl.[5] .............................................. C07C 101/72
[52] U.S. Cl. ...................................... 560/045; 560/49; 560/50; 564/168
[58] Field of Search .............................. 560/45, 49, 50; 564/168; 514/535, 536

[56] References Cited

U.S. PATENT DOCUMENTS

| | | | |
|---|---|---|---|
| 2,392,361 | 1/1946 | Britton et al. | 260/474 |
| 3,148,934 | 9/1964 | Brookens et al. | 8/4 |
| 3,636,077 | 1/1972 | Stauffer | 260/471 R |
| 3,676,471 | 7/1972 | Eggensperger et al. | 260/410 |
| 3,751,563 | 8/1973 | Richardson | 424/60 |
| 3,936,419 | 2/1976 | Wang | 514/972 |
| 3,937,810 | 2/1976 | Mathur et al. | 424/62 |
| 3,980,617 | 9/1976 | Jacquet et al. | 260/47 UA |
| 4,002,733 | 1/1977 | Degen et al. | 424/59 |
| 4,115,547 | 9/1978 | Degen et al. | 424/60 |
| 4,264,581 | 4/1981 | Kerkhof et al. | 424/60 |
| 4,387,089 | 6/1983 | Depolo | 424/59 |
| 4,421,739 | 12/1983 | Bouillon et al. | 424/47 |
| 4,584,190 | 4/1986 | Tejima et al. | 424/59 |

FOREIGN PATENT DOCUMENTS

| | | |
|---|---|---|
| 2706782 | 9/1977 | Fed. Rep. of Germany. |
| 2285853 | 4/1976 | France. |
| 2383904 | 10/1978 | France. |
| 2456731 | 12/1980 | France. |
| 57-80356 | 5/1982 | Japan. |
| 61-78715 | 9/1984 | Japan. |
| 350461 | 1/1961 | Switzerland. |
| 1186818 | 4/1970 | United Kingdom. |
| 1291917 | 10/1972 | United Kingdom. |
| 1370236 | 10/1974 | United Kingdom. |
| 1407670 | 9/1975 | United Kingdom. |
| 1473483 | 5/1977 | United Kingdom. |
| 1557580 | 12/1979 | United Kingdom. |
| 2028131 | 3/1980 | United Kingdom. |
| 2149789 | 6/1985 | United Kingdom. |

OTHER PUBLICATIONS

Sayre, Agin, LeVee & Marlow, "a Comparison of in vivo and in vitro Testing of Sunscreen Formulas", Photochemistry and Photobiology, vol. 29, No. 3, (Mar., 1979), pp. 559–566.

Grammaticakis, "Contribution à l'étude de l'absorption dans l'U.-V. moyen et le visible de queleques aldéhydes et cétones aromatiques ainsi que certains de leurs dérivivés fonctionnels, (premier mémoire)", Bulletin de La Societe Chimique de France, Article 164 (May 12, 1953), pp. 821–826.

Grammaticakis, "Contribution à l'étude de l'absorption dans l'U.-V. moyen et le visible des composés carbonylés aromatiques et de leurs dérivés (deuxieme mémoire)", Bulletin de La Societe Chimique de France, Article 174, (May 27, 1953), pp. 865–872.

Temchin et al., Vysokomol. Soedin., Serial A, 15(5), pp. 1038–1048 (1973); (CAS 79:79679r).

Temchin et al., Mater. Plast. Elastomeri, 1975, pp. 41–44 (1975); (CAS 83:60222x).

Volkotrub et al., Plast. Massy, 1974 (9), p. 76 (1974); (CAS 82:86978c).

Balogh et al., Plasty. Kauc, 14(7), pp. 204–207 (1977); (CAS 87:185422b).

Jacquet et al., Rev. Gen. Caoutch. Plast., 54 (575), pp. 85–88 (1977); (CAS 89:6867x).

Akin et al., Toxicol. Appl. Pharmacol., 49 (2), pp. 219–224 (1979).

Sayre et al., Photochem. Photobiol., 29(3), pp. 559–566 (1979).

Cumpelik; J. Soc. Cosmet. Chem., 31(7), pp. 361–366 (1980).

Destrade et al., Mol. Cryst. Liq. Cryst., 59 (3–4), pp. 273–288, (1980); (CAS 93:58557y).

Primary Examiner—Paul J. Killos
Attorney, Agent, or Firm—Milton B. Graff, IV; Steven J. Goldstein; Jack D. Schaeffer

[57] ABSTRACT

The present invention relates to novel chromophore-containing compounds useful as sunscreen agents which have the ability to absorb both UVA and UVB wavelength radiation. These compounds comprise a specific type of UVA-absorbing chromophore covalently bonded to a specific type of UVB-absorbing chromophore. The chromophore moieties are covalently bonded together such that the electron systems of these moieties are directly coupled to thereby form a new chromophore.

The present invention further relates to sunscreen compositions containing the hereinbefore described type of sunscreen agents. Furthermore, the present invention relates to methods for protecting the skin or humans or lower animals from the effects of UVA and UVB wavelength radiation. This method comprises topically applying to the skin an effective coating of a sunscreen composition of the present invention.

17 Claims, No Drawings

NOVEL CHROMOPHORES, SUNSCREEN COMPOSITIONS AND METHODS FOR PREVENTING SUNBURN

CROSS-REFERENCE TO RELATED APPLICATION

This application is a continuation-in-part of application Ser. No. 879,724 filed June 27, 1986.

BACKGROUND OF THE INVENTION

The present invention relates to novel chromophore compounds useful as sunscreen agents. These chromophore compounds have the ability to strongly absorb sunlight in both the UVA and UVB wavelength range. The present invention further relates to novel skin protection compositions which are effective at protecting skin from both the UVA and UVB wavelength radiation component of sunlight. Finally, the present invention also relates to methods for protecting the skin from the effects of UVA and UVB wavelength irradiation, such as sunburn and sun-induced aging of the skin.

The damaging effects of sunlight on skin are well documented. In spite of this, people are forced to be in the sun for long periods of time due to their occupations. Others are in the sun for long periods through their leisure time activities and/or a desire to have a tanned appearance.

The major short term hazard of prolonged exposure to sunlight is erythema (i.e., sunburn). The 290 to 320 nanometer wavelength ultraviolet radiation range, which is designated by the cosmetic industry as being the "UVB" wavelength range, is the most effective type of UV radiation for producing erythema. The 320 to 400 nanometer wavelength ultraviolet radiation range, which is designated by the cosmetic industry as being the "UVA" wavelength range, also produces erythema.

In addition to the short term hazard of erythema caused by UVA and UVB sunlight, there are also long term hazards associated with this UV radiation exposure. One of these long term hazards is malignant changes in the skin surface. Numerous epidemiologic studies have been conducted, and the results demonstrate a strong relationship between sunlight exposure and human skin cancer. Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity. The adverse effects associated with exposure to UVA and UVB wavelength radiation are more fully discussed in DeSimone, "Sunscreen and Suntan Products", *Handbook of Nonprescription Drugs*, 7th Ed, Chapter 26, pp. 499-511 (American Pharmaceutical Association, Washington, D.C.; 1982); Grove and Forbes, "A Method for Evaluating the Photoprotective Action of Sunscreen Agents Against UV-A Radiation", *International Journal of Cosmetic Science*, 4, pp. 15-24 (1982); and U.S. Pat. No. 4,387,089, to DePolo, Issued June 7, 1983; the disclosures of all of which are incorporated herein by reference. Hence, although the immediate effects of ultraviolet radiation may be cosmetically and socially gratifying, the long-term effects are cumulative and potentially serious.

Sunscreen compositions comprising mixtures of molecules which absorb at different UV wavelengths and which thereby protect the skin are known in the art. For example, U.S. Pat. No. 4,264,581, to Kerkhof et al (issued Apr. 28, 1981), discloses a sunscreen composition containing a mixture of 2-ethylhexyl dimethyl-para-amino benzoate and 2-hydroxy-4-methoxy-benzophenone; U.S. Pat. No. 3,751,563, to Richardson (issued Aug. 7, 1973), discloses a sunscreen composition containing a mixture of 2-ethoxyethyl para-methoxycinnamate, amyl para-dimethylamino benzoate, homomenthyl salicylate, and 2-hydroxy-4-methoxy-benzophenone; and U.S. Pat. No. 3,636,077, to Stauffer (issued Jan. 18, 1972), discloses sunscreen compositions containing salts of 5-benzoyl-4-hydroxy-2-methoxy benzene sulfonic acid and 4-aminobenzoic acids or esters.

Notwithstanding the foregoing developments, there remains a continuing need to identify new compounds and compositions which are effective for protecting the skin from ultraviolet radiation in both the UVA and UVB radiation ranges. It is accordingly an object of the present invention to provide new chromophore compounds which are effective sunscreening agents for both UVA and UVB radiation, as well as sunscreen compositions containing these chromophore compounds. It is a further object of the present invention to provide methods for protecting the skin of humans or lower animals from the effects of exposure to UVA and UVB wavelength radiation by employing sunscreening compounds and compositions of the present invention.

It is an additional object of the present invention to provide new chromophore compounds which have broad and strong absorption spectra throughout both the UVA and UVB radiation range. It is a further object of the present invention to provide sunscreening agents and compositions which are not readily absorbed by the skin; which have increased sunscreen protection and decreased chance for allergy, irritation, or toxicity problems resulting from use; and which are resistant to rub off. A still further object is to provide sunscreen agents and compositions which provide a constant and even protection against both UVA and UVB radiation; which are cosmetically acceptable; and which are readily formulated into sunscreen compositions.

These and other objects will become readily apparent from the detailed description which follows.

SUMMARY OF THE INVENTION

The present invention relates to novel chromophore-containing sunscreen compounds useful as sunscreen agents, which compounds are effective for absorbing ultraviolet radiation in both the UVA and UVB wavelength range. These new compounds are formed by covalently linking a selected UVA-absorbing chromophore moiety and a selected UVB-absorbing chromophore moiety together in the same molecule. These chromophore moieties are liked such that the electron systems of the chromophore moieties are directly coupled via this covalent linkage to thereby form a new chromophore-containing compound.

The present invention further relates to sunscreen compositions. These compositions comprise a pharmaceutically-acceptable sunscreen carrier and a chromophore compound generally characterized by having both a UVA-absorbing chromophore moiety and a UVB-absorbing chromophore moiety. Again, the chromophore moieties are covalently linked such that the electron systems of these moieties are directly coupled via the covalent linkage.

Finally, the present invention also relates to methods for protecting the skin of humans or lower animals from the effects of UVA and UVB wavelength radiation, such as sunburn and suninduced aging of the skin. Such methods comprise topically applying to the human or lower animal an effective coating of a sunscreen agent useful in the present invention.

DETAILED DESCRIPTION OF THE INVENTION

Sunscreen agents

The sunscreen agents useful in the present invention are novel chromophore-containing compounds which are derived from two chromophore moieties that have different ultraviolet radiation absorption spectrums. In particular, one of the chromophore moieties absorbs predominantly in the UVB radiation range, and the other absorbs strongly in the UVA radiation range. Further, these molecules have the chromophore moieties linked in the molecule by covalent bonding, with this covalent linkage permitting the electron systems of the chromophore moieties to be directly coupled through the linkage to thereby form a new chromophore.

More particularly, one of the chromophore moieties is characterized as being effective for strongly absorbing radiation in the UVA range when that chromophore moiety is isolated in an independent molecule. The other chromophore moiety is charcterized as being effective for absorbing radiation predominantly within the UVB range when that chromophore moiety is isolated in an independent molecule. These two chromophore moieties are covalently joined such that the electron systems of these chromophore moieties are directly coupled, thereby creating the new chromophore-containing compounds of the present invention. Thus, the sunscreen agents useful in the present invention are compounds having the general structure:

X—B—Z.

In this general structure, the X group is a UVA-absorbing chromophore that is a substituted, carbonyl-containing, aromatic ring-containing moiety. This UVA-absorbing moiety when isolated as an independent chromophore would exhibit at least one absorption maximum (designated herein as λmax, and described more fully hereinafter) within the wavelength range of from about 320 to about 400 nm. This absorption maximum would exhibit a molar absorptivity value (designated herein as "ε", and calculated as described hereinafter) of at least about 9,000, preferably at least about 20,000, and most preferably at least about 30,000.

The Z group in the above general structure is a UVB-absorbing chromophore that is a substituted, carbonyl-containing, aromatic ring-containing moiety. This UVB-absorbing moiety, when isolated as an independent chromophore, would exhibit a molar absorptivity value of at least about 4,000, preferably at least about 15,000, and most preferably at least about 25,000, for at least one wavelength within the range of from about 290 to about 320 nm. Preferably, when present as the sole chromophore in a molecule as hereinafter defined, the Z group exhibits at least one absorption maximum λmax within the range of from about 290 to about 320 nm. This absorption maximum preferably has a molar absorptivity value ε of at least about 4,000, more preferably at least about 15,000, and most preferably at least about 25,000. Finally, when present as the sole chromophore in a molecule as hereinafter defined, the Z group furthermore should not exhibit a λmax having an ε greater than about 9,000 for any wavelength above about 320 nm.

Finally, in the above general structure the B group is a chemical bond or linking moiety which covalently bonds the two X and Z chromophore moieties such that the electron systems of these chromophores are directly coupled, i.e., electrons are shared. Preferred is B selected from a single bond, or atoms or groups of atoms which have free electrons which may be shared with both chromophore moieties, such as —O— and —NR— (wherein R is H, straight or branched chain alkyl having from about 1 to about 20 carbon atoms, $(CH_2CH_2O)_m$—H, or $(CH_2CH(CH_3)O)_m$—H, wherein m is an integer from 1 to about 8, and preferably m=1 to about 3). Most preferred is B being —NH— and, especially, —O—.

The sunscreen agents of the present invention preferably absorb light in the visible wavelength range (i.e., above about 400 nm) only weakly or not at all. The compounds are therefore either only lightly colored (e.g., light yellow or cream colored) or are essentially white. This is desirable for cosmetic reasons. Thus, the sunscreen agents preferbly do not have an ε of greater than about 500 for any wavelength above about 400 nm, and most preferably the ε is essentially zero for any wavelength above about 400 nm.

It is further preferred that the compounds of the present invention be lower molecular weight compounds, preferably having a molecular weight of less than about 2,500, and most preferably less than about 1,000. Furthermore, the compounds are preferably liquids above about 10° C.

Specifically, examples of suitable X chromophore moieties useful in the sunscreen compounds of the present invention include

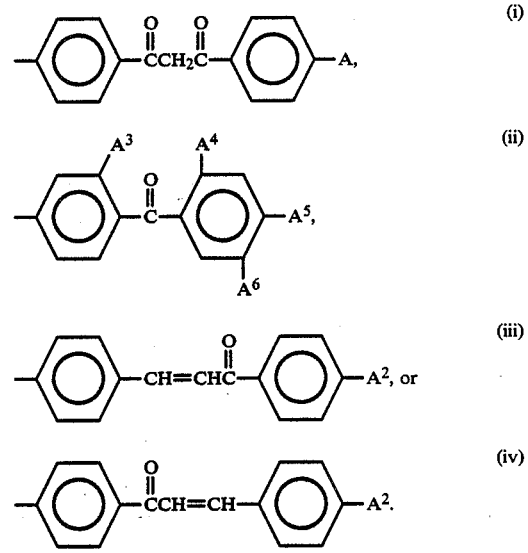

In all the preceding formulae, each A is a substituent independently selected from the group consisting of R, —OR, —NR$_2$, or —SO$_3$H, or its pharmaceutically-acceptable salt or ester; each A$^2$ is independently —OR or —NR$_2$; each A$^3$ is independently H or OH; each A$^4$ and $A^5$ are, independently, R or OR, and wherein further either $A^3$ or $A^4$ must be OH; each $A^6$ is independently H or —$SO_3H$, or its pharmaceutically-acceptable salt or ester; and each R is independently H, straight or branched chain alkyl having from about 1 to about 20 carbon atoms, $(CH_2CH_2O)_m$—H, or $(CH_2CH(CH_3)O)_m$—H, wherein m is an integer from 1 to about 8, and preferably m=1 to about 3.

Preferred as the X chromophore moiety are the groups

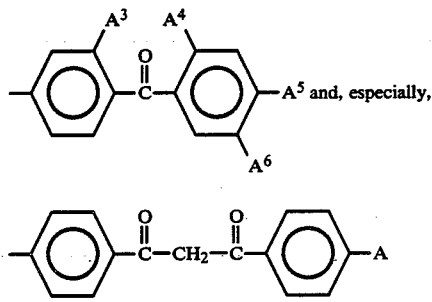

Preferably, either $A^3$ or $A^4$ is OH, with the other group being H; $A^5$ is R; and $A^6$ is H. Most preferably, $A^3$ is OH, and $A^4$, $A^5$ and $A^6$ are H. A is preferably R, and most preferably A is H.

Also specific examples of the Z chromophore moieties useful in the sunscreen compounds of the present invention include:

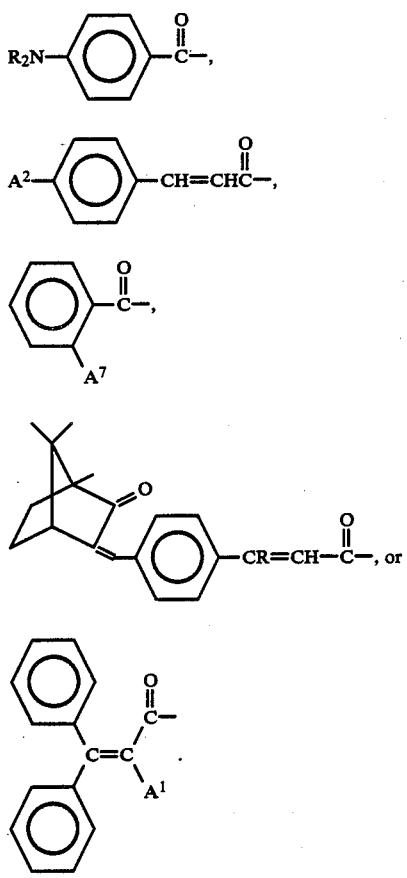

In these preceding formulae, each $A^1$ is independently —CN or —$CO_2R^1$; each $A^7$ is independently —OR or —$O_2C$—$R^1$, except that both $A^7$ and $A^3$ (described hereinbefore for the X groups) are not —OH; each $R^1$ is independently straight or branched chain alkyl having from about 1 to about 20 carbon atoms; and the $A^2$ and R substituent groups are as described hereinbefore for the substituted X groups.

Preferred as the Z chromophore moiety are the groups

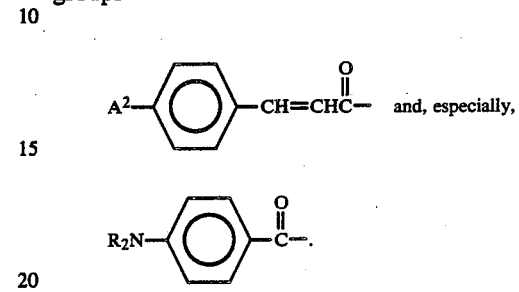

Preferably, —$NR_2$ is —$NR^1_2$. Both $R^1$ groups may be different alkyl groups. Particularly preferred is one $R^1$ group having more than about 2 carbon atoms (especially branched-chain alkyl groups, e.g., 2-ethyl-hexyl), the other $R^1$ group being methyl or ethyl, especially methyl. Alternatively, both $R^1$ groups are the same alkyl group, preferably 2-ethylhexyl. Also preferred is $A^2$ being —OR or —$NR_2$ (preferably the —$NR_2$ is —$NR^1_2$ as described hereinbefore). Most preferred $A^2$ is —$OCH_3$, —$OCH_2CH_3$, OH, or —$NR^1_2$ (wherein one $R^1$ group has more than about 2 carbon atoms, especially branched-chain alkyl, and the other $R^1$ group is methyl or ethyl, especially methyl).

Preferred sunscreen agents of the present invention have the general structures:

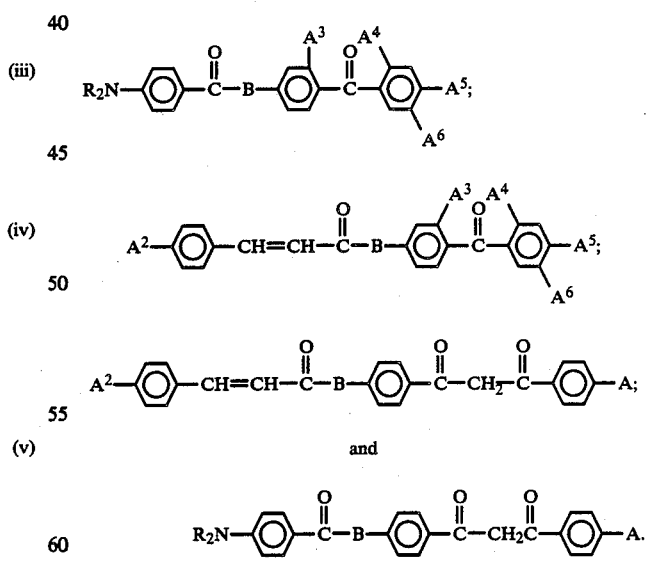

Especially preferred are the last two structures, with the last structure being most preferred. The B group and substituents on these structures are preferably as described hereinbefore.

Specific sunscreen agents of the present invention include, for example:

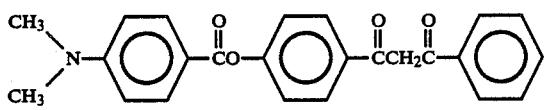

4-N,N-dimethylaminobenzoic acid ester with 4-hydroxydibenzoylmethane ("Compound 1");

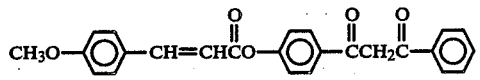

4-methoxycinnamic acid ester with 4-hydroxydibenzoylmethane ("Compound 2");

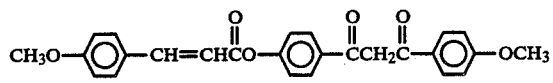

4-methoxycinnamic acid ester with 4-hydroxy-4'-methoxydibenzoylmethane ("Compound 3");

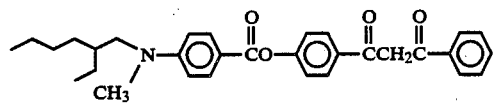

4-N,N-(2-ethylhexyl)methylaminobenzoic acid ester with 4-hydroxydibenzoylmethane ("Compound 4"); and

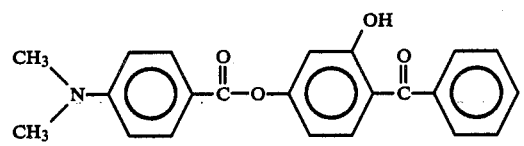

4-N,N-dimethylaminobenzoic acid ester with 2,4-dihydroxybenzophenone ("Compound 5");

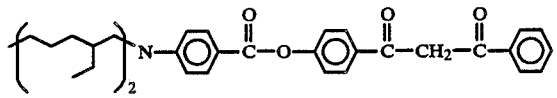

N,N-di(2-ethylhexyl)-4-aminobenzoic acid ester with 4-hydroxydibenzoylmethane (Compound 6"); and

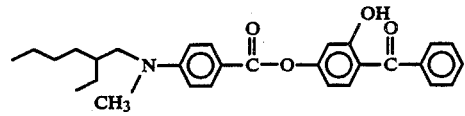

4-N,N-(2-ethylhexyl) methylaminobenzoic acid ester with 2,4-dihydroxybenzophenone ("Compound 7").

The sunscreen agents of the present invention can be prepared from commercially-available, chromophore-containing molecules. Typically, the synthesis of the sunscreen agents will be achieved by an esterification or amidation reaction. Synthesis techniques which are generally applicable for synthesizing sunscreen agents of the present invention are taught, for example, in U.S. Pat. No. 4,002,733, issued Jan. 11, 1977, to Degen at al.; and in U.S. Pat. No. 4,115,547, issued Sept. 19, 1978, to Degen et al.; the disclosures of both these patents being incorporated herein by reference. Representative procedures for synthesizing the sunscreen agents of the present invention are provided in the Examples hereinafter.

The term "pharmaceutically-acceptable salts and esters", as used herein, means those ester and salt forms of the sunscreen agents which are acceptable from a toxicity viewpoint. Pharmaceutically-acceptable salts include alkali metal (e.g., sodium and potassium), alkaline earth metal (e.g., calcium and magnesium), nontoxic heavy metal (e.g., stannous and indium), and ammonium and low molecular weight substituted ammonium (e.g., mono-, di-, tri- and tetra-substituted amine which are substituted with methyl and/or ethyl) salts. Preferred are the sodium, potassium, and ammonium salts. Pharmaceutically acceptable esters include straight or branched chain alkyl ester having from 1 to about 20 carbon atoms, preferably the methyl or ethyl ester.

The term "independent chromophore", as used herein, means the chromophore moiety (i.e., either the X or Z group) when it is bonded to —O—$R^2$ (wherein $R^2$ represents a short chain alkyl group, e.g., methyl or ethyl; preferably methyl) rather than the chromophore moiety being bonded to the B linking moiety within the X—B—Z compound. For example, independent chromophores of Compound 5 described hereinbefore are the ethyl ester of 4-N,N-dimethylaminobenzoic acid and 2-hydroxy-4-methoxybenzophenone. Also as an example, independent chromophores of Compound 4 described hereinbefore are the methyl ester of 4-N,N-(2-ethylhexyl)methylaminobenzoic acid and 4-methoxydibenzoylmethane.

The term "molar absorptivity value", as used herein, is a quantitative measure of the ability of a molecule to absorb ultraviolet light at a specified wavelength. The molar absorptivity value is expressed at a particular wavelength of light as the molar absorption coefficient (represented herein by "$\epsilon$" which is expressed in units of liter/mole cm), which is calculated by the equation:

$$\epsilon = \frac{A}{lc}$$

wherein "l" is the path length (in centimeters) of the absorbing media through which the light passes; "c" is the concentration of the chromophore molecule (in moles per liter); and "A" is the "absorbance". The absorbance is calculated from the observed difference in the intensity of the particular wavelength of light before and after passing through the chromophore-molecule-containing absorbing media. Thus, the absorbance is calculated by the equation:

$$A = \log_{10} \frac{Io}{I}$$

wherein "$I_0$" is the intensity of a particular wavelength of incident radiation on an absorbing path; and "I" is the intensity of the same particular wavelength of transmitted radiation which has passed through the absorbing path.

The calculation of the molar absorptivity value for a particular wavelength of light is well-known in the art, and is taught in more detail in *Atlas of Spectral Data and Physical Constants for Organic Compounds,* 2nd Ed., Vol. 1, pp. 399–408 (Grasselli and Ritchey, Editors;

CRC Press, Inc., Cleveland, Ohio, 1975), the disclosures of which are incorporated herein by reference. Instruments useful for making the intensity measurements for the calculation of the molar absorptivity value are also well-known in the art (eg., Varion DMS-100 L and Beckman DU-7). Molar absorptivity values for representative compounds of the present invention are provided in the Examples hereinafter.

The term "absorption maximum", as used herein, means a wavelength of radiation at which the chromophore-containing molecule has the greatest molar absorptivity value relative to wavelengths immediately above and below the absorption maximum wavelength. Thus, in the typical spectrum of UV-radiation absorption, the absorption maximum are easily identified as peaks in the graph of the spectrum generated by the instrument measuring the UV absorption. Absorption maximum (designated herein as $\alpha max$) are provided for representative sunscreen compounds of the present invention in the Examples hereinafter.

The sunscreen agents useful in the present invention have several desirable properties relative to a simple mixture of a UVA-absorbing molecule with a UVB-absorbing molecule. Particularly beneficial is the large values and broad absorption spectra of the novel chromophores of the present invention. This permits the use of lower amounts of sunscreen agent of the present invention, relative to a mixture of molecules, to achieve the same quantity of sunscreen protection. Furthermore, this translates into better sunscreen protection throughout the entire UVA and UVB radiation range.

An additional benefit from the present invention is the certainty of providing both UVA and UVB protection at the same site on the skin. A mixture of molecules may lack this uniformity due to non-uniform distribution onto the skin surface and/or selective penetration by one type of molecule through the skin versus the other type of molecule. A related benefit is that the sunscreen agents of the present invention provide a constant relative proportion of UVA to UVB protection. A mixture of chromophore molecules may not maintain a constant relative proportion of UVA to UVB protection because one chromophore may be more readily lost from the skin (e.g., by a higher rate of rub-off or skin penetration) than the other chromophore. Another benefit is that the sunscreen agents of the present invention are absorbed more slowly by the skin than mixtures of the independent chromophores. This translates into longer duration of protection for the skin, and less potential for skin irritation resulting from absorption by the skin. The ability of the sunscreen compounds of the present invention, and of mixtures of independent chromophores, to absorb UV radiation may be measured by in vitro methods known generally in the art, such as those taught in Sayre et al., "A Comparison of in vivo and in vitro Testing of Sunscreening Formulas", *Photochem. Photobiol.*, 29, 559–566 (1979), the disclosures of which are incorporated herein by reference. Some of the compounds of the present invention may also be more resistant to wash-off by water from sweat or swimming.

The sunscreen agent of the present invention typically comprise from about 0.1% to about 99.9% by weight of the sunscreen compositions of the present invention, preferably from about 1% to about 20%, and most preferably from about 5% to about 15%.

Pharmaceutically-acceptable Sunscreen Carriers

In addition to a sunscreen agent as described hereinbefore, the sunscreen compositions of the present invention essentially contain a pharmaceutically-acceptable sunscreen carrier. The term "pharmaceutically-acceptable sunscreen carrier", as used herein, means one or more substantially non-irritating compatible filler diluents which are suitable for topical application to the skin of a human or lower animal. The term "compatible", as used herein, means that the components of the carrier must be capable of being comingled with the sunscreen agent, and with each other, in a manner such that there is no interaction which would substantially reduce the efficacy of the composition during use for protecting the skin from the effects of UVA and UVB wavelength radiation. Pharmaceutically-acceptable sunscreen carriers must, of course, be of sufficiently high purity and sufficiently low toxicity to render them suitable for topical administration to the human or lower animal.

The sunscreen compositions of the present invention contain pharmaceutically-acceptable sunscreen carriers selected as appropriate for the formulation desired. For example, it is possible to prepare sunscreen compositions of the present invention in the form of organic solvent solutions, aqueous emulsions, gels, or aerosol formulation. Preferred are sunscreen compositions of the present invention formulated as aqueous emulsions. The pharmaceutically-acceptable sunscreen carriers useful in the compositions of the present invention include, for example, water, oils, fats, waxes, synthetic polymers, emulsifiers, surfactants, perfumes, dyes, preservatives, artificial tanning agents (e.g., dihydroxyacetone), and conventional sunscreening agents (e.g., octyl N,N-dimethyl-para-aminobenzoate; 2-hydroxy-4-methoxybenzophenone).

Water is typically the major component of the sunscreen compositions of the present invention. Generally, water is present at a level of from about 50% to about 99% by weight of the composition, preferably from about 70% to about 96%, and most preferably from about 75% to about 85%.

Emulsifiers are preferably included in the sunscreen compositions of the present invention, preferably comprising from about 1.5% to about 10% by weight of the composition, and most preferably from about 2% to about 5%. Preferred emulsifiers are anionic or nonionic although other types may also be used. Suitable emulsifiers are disclosed in, for example, U.S. Pat. No. 3,755,560, issued Aug. 28, 1973, to Dickert et al.; U.S. Pat. No. 4,421,769, issued Dec. 20, 1983, to Dixon et al.; and McCutcheon's *Detergents and Emulsifiers*, North American Edition, 1983; with the disclosures of these references being incorporated herein by reference.

Types of emulsifiers useful in the sunscreen compositions of the present invention include ethoxylated fatty acids, ethoxylated esters, ethoxylated ethers, ethoxylated alcohols, phosphated esters, polyoxyethylene fatty ether phosphates, fatty acid amides, acyl lactylates, soaps and mixtures thereof. Fatty alcohols such as cetyl and stearyl alcohol, and cetearyl alcohol are also regarded as emulsifiers for purposes of the present invention.

Examples of such emulsifiers include polyoxyethylene (8) stearate, myristyl ethoxy (3) myristate, polyoxyethylene (100) monostearate, lauric diethanolamide, stearic monoethanolamide, hydrogenated vegetable glycerides, sodium steroyl-2-lactylate and calcium stearoyl-2-lactylate. Soaps are also acceptable emulsifiers. The soaps may be formulated in situ in processing the compositions and are preferably alkali metal or triethanolamine salts of long-chain fatty acids. Such soaps include sodium stearate, triethanolamine stearate and the similar salts of lanolin fatty acids.

Also preferred for use in the compositions of the present invention is a copolymer of ethylene and acrylic acid. These monomers:

Ethylene: $CH_2=CH_2$

Acrylic Acid: 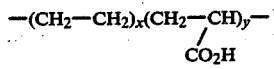

are present in polymeric form as follows:

$$-(CH_2-CH_2)_x(CH_2-CH)_y-$$
$$\phantom{-(CH_2-CH_2)_x(CH_2-}CO_2H$$

wherein the ratio of x:y is from about 1:24 to about 1:9. The weight average molecular weight is from about 3,500 to about 4,500, preferably from about 4,000 to about 4,300.

The compositions of the present invention may also contain in addition to the aforementioned components, a wide variety of additional oil soluble materials and/or water soluble materials.

Among the oil soluble materials are non-volatile silicone fluids such as polydimethyl siloxanes with viscosities ranging from about 10 to about 100,000 centistokes at 25° C. These siloxanes are available from Dow Corning Corporation as the Dow Corning 200 series.

Other oil soluble materials include fatty acid alcohols such as cetyl alcohol and stearyl alcohol; esters such as cetearyl palmitate, lauryl myristate and isopropyl palmitate; oil such as castor oil, jojoba oil, cottonseed oil, peanut oil and sesame oil; waxes such as petrolatum, ceresin wax, carnauba wax, beeswax, and castor wax; lanolin, its derivatives and components such as acetylated lanolin, lanolin alcohols and lanolin fatty acids. Sterols such as cholesterol and phytosterol are also useful herein.

These optional oil phase materials may individually comprise up to about 20% by weight of the total sunscreen composition, preferably up to about 10%.

Additional water soluble materials may also be present in the compositions of this invention. Included are humectants such as glycerine, sorbitol, propylene glycol, alkoxylated glucose and hexanetriol; tyrosine; thickening agents such as carboxyvinyl polymers (Carbopols ®-offered by B. F. Goodrich Company, such polymers are described in detail in U.S. Pat. No. 2,798,053, issued July 2, 1957 to Brown, incorporated herein by reference); ethyl cellulose, polyvinyl alcohol, carboxymethyl cellulose, vegetable gums and clays such as Veegum ®(magnesium aluminum silicate, R. T. Vanderbilt, Inc.); proteins and polypeptides; preservatives such as the methyl, ethyl, propyl and butyl esters of hydroxybenzoic acid (Parabens-Mallinckrodt Chemical Corp.), EDTA, methylisothiazolinone and imidazolidinyl ureas (Germall 115-Sutton Laboratories); and an alkaline agent such as sodium hydroxide or potassium hydroxide to neutralize, if desired, part of the fatty acids or thickeners which may be present.

The water phase materials may individually comprise up to about 20% by weight of the total sunscreen composition, preferably up to about 10%.

The present compositions may also contain agents suitable for aesthetic purposes such as perfumes and/or dyes.

The pH of the sunscreen compositions herein is preferably in the range of from about 4.5 to about 9.

For an aqueous emulsion sunscreen composition of the present invention, the mean particle size of the dispersed oil phase materials (e.g., sunscreen agent, polymer, perfumes, etc.) dispersed in the aqueous phase may be in the range of from about 5 to about 10 microns with greater than about 75% of the particles being less than about 12 microns.

The pharmaceutically-acceptable sunscreen carriers, in total, typically comprise from about 0.1% to about 99.9% by weight of the sunscreen compositions of the present invention, preferably from about 80% to about 99%, and most preferably from about 85% to about 95%.

The compositions of the present invention may be prepared using the method described in the examples hereinafter.

Method for Preventing Sunburn

The present invention further relates to a method for protecting the skin of humans or lower animals from the effects of UVA and UVB wavelength radiation, such as sunburn and premature aging of the skin. Such a method comprises topically applying to the human or lower animal an effective coating of a sunscreen agent of the present invention, or, preferably, of a sunscreen composition of the present invention. The term "effective coating", as used herein, means a film of sunscreen agent sufficient to substantially reduce the amount of UVA and UVB wavelength light which reaches the skin's surface. Typically, an effective coating of the skin is from about 0.5 mg sunscreen agent of the present invention/$cm^2$ skin to about 5 mg sunscreen agent of the present invention/$cm^2$ skin.

The following examples further describe and demonstrate the preferred embodiments within the scope of the present invention. The examples are given solely for the purpose of illustration, and are not to be construed as limitations of the present invention since many variations thereof are possible without departing from its spirit and scope.

EXAMPLE 1

Synthesis of Compound 4

(a) Synthesis of 4-N,N-(2-ethylhexyl)methylaminobenzoic acid

A 1000 mL, 3 necked, round-bottomed flask equipped with an overhead stirrer, dropping funnel, and reflux condenser is charged with 4-N-methylaminobenzoic acid (25.0 g, 0.165 mol Aldrich Chemical Co., Milwaukee, WI), 130 mL of toluene, glacial acetic acid (40.0 g), and zinc dust (42.5 g, 0.65 g atom). This mixture is heated to reflux with stirring at which time a dropwise addition of 2-ethylhexanol (84.6 g, 0.66 mol) is begun. After the addition is completed, the reaction mixture is refluxed for 16 hours. TLC analysis (silica gel, 50/50 hexane/acetone) shows that not all of the acid is reacted. An additional 7.0 g of zinc dust and 2 mL of glacial acetic acid is added. After 2 hours of additional reflux, TLC analysis shows the starting acid to be consumed. The hot solution is filtered through a Celite ® filter cake on a medium sintered glass funnel and washed with 100 mL of hot toluene. The filtrate is poured into a separatory funnel containing 200 mL of water and 500 mL of chloroform. The mixture is brought to pH approximately 1 with concentrated hydrochloric acid. After shaking intimately, the chloroform layer is drained off and the aqueous layer is extracted with chloroform (3×150 mL). The combined chloroform extracts are washed with 150 mL of brine and dried over magnesium sulfate. After filtration and removal of the solvents by rotary evaporation (0.1 Torr, 100° C. water bath), 40.4 g of a light brown waxy solid is obtained. This material is recrystallized from 120 mL of 90% ethanol to yield 30.2 g of a fluffy white solid, m.p. 55.5°–57.5° C. Anal. calcd. for $C_{16}H_{25}O_2N$: C, 72.96; H, 9.57; O, 12.15; N, 5.32. Found: C, 73.11; H, 9.62; O, 12.28; N, 5.23.

Alternatively, N-(2-ethylhexyl)-N-methyl-4-aminobenzoic acid can be prepared by the following method. Ethyl 4-aminobenzoate is dissolved in 1:1 acetic acid/ethanol with 2-ethyl hexanal. Then 10% Pd on Carbon (2 kg benzoate/75 g catalyst) is added. This mixture is placed under hydrogen at room temperature for one hour. The reaction is then determined to be complete by TLC. An excess of 40% aqueous formaldehyde is added and the reaction again placed under hydrogen at 30°–35° C. for one hour. The reaction is complete by TLC. The reaction mixture is then filtered through Celite and the solvents removed. The resulting material is partitioned between water and methylene chloride. The methylene chloride layer is then washed with saturated sodium bicarbonate. The resulting methylene chloride layer is then dried over magnesium sulfate and the volatiles are removed after filtration to give the desired product as the ethyl ester. This material is placed in 12 volumes of ethanol/water (65:35) per weight of ethyl ester. Two mole equivalents of sodium hydroxide are added and the mixture refluxed for two hours. The reaction is then complete by TLC. Most of the ethanol is removed and more water added followed by the hydrochloric acid. The resulting desired carboxylic acid then precipitates. The total process is close to quantitative. Recrystalization of the product is in 2 kg acid per 4.5 liters of ethanol. About a 70% recovery of material is observed.

(b) Synthesis of 4-hydroxydibenzoylmethane

A 1000 mL, 3 necked, round-bottomed flask equipped with an overhead stirrer, dropping funnel, and reflux condenser is charged with sodium hydride 80% oil dispersion (12.0 g, 0.40 mol) which is washed twice with hexane. Next, 200 mL of freshly distilled glyme is added and the slurry heated to reflux with stirring. A solution of 4-hydroxyacetophenone (13.62 g, 0.10 mol) dissolved in 100 mL of glyme is added dropwise. The reaction mixture is allowed to reflux for 45 minutes after the addition. Next, a solution of methyl benzoate (13.62 g, 0.10 mol) dissolved in 100 mL of glyme is added dropwise. The reaction mixture is allowed to reflux for 16 hours, after which time most of the glyme was distilled off at aspirator pressure. The pot residue is cooled in an ice bath and 300 mL of ether is added followed by the cautious addition of 200 mL of water. The mixture is poured into a separatory funnel, shaken intimately, and the aqueous layer removed. The ether layer is washed with cold water (2×200 mL) followed by 100 mL of cold 1% aqueous NaOH. The combined aqueous layers are carefully poured onto a mixture of 400 g of ice plus 90 mL of concentrated HCl. The yellowish green solid that precipitates is collected by suction filtration and washed with a little cold water. This material is recrystallized from 95% ethanol to yield 13.1 g of a yellow solid, m.p. 153°–156° C. Anal. calcd. for $C_{15}H_{12}O_3$: C, 74.99; H, 5.03; O, 19.98. Found: C, 74.72; H, 5.02; O, 19.80.

(c) Synthesis of Compound 4

A 50 mL, round-bottomed flask equipped with a magnetic stir bar is charged with 4-N,N-(2-ethylhexyl)-methylaminobenzoic acid (1.22 g, 4.62 mmol), 4-hydroxydibenzoylmethane (1.11 g, 4.62 mmol), and 10 mL DMF. To the golden solution is added 9.2 mL of polyphosphate ester and an additional 10 mL of DMF. The reaction mixture is heated to 85° C. for 40 hours. The deep red reaction mixture is poured into 25 mL of cold water to yield a yellow precipitate which is collected by suction filtration and washed with a little water. This material is recrystallized from ethanol to give 1.45 g of a light yellow solid, m.p. 90°–91.5° C. Anal calcd for $C_{31}H_{35}O_4N$: C, 76.68; H, 7.26; O, 13.18; N, 2.88. Found: C, 76.13; H, 7.50; O, 13.59; N, 2.84.

The UV spectrum of Compound 4 (isopropanol solution) exhibits a λmax=338 nm (ε=51,350).

EXAMPLE 2

Synthesis of Compound 5

By a procedure analogous to that described hereinbefore in Example 1, Compound 5 is synthesized from 4-N,N-dimethylaminobenzoic acid and 2,4-dihydroxybenzophenone (both from Aldrich Chemical Company; Milwaukee, WI). The UV spectrum of Compound 5 (isopropanol solution) exhibits a λmax=321.5 (ε=42,490).

EXAMPLE 3

Synthesis of Compound 1

By a procedure analogous to that described hereinbefore in Example 1, Compound 1 is synthesized from 4-N,N-dimethylaminobenzoic acid (Aldrich Chemical Company; Milwaukee, WI) and 4-hydroxydibenzoylmethane (which is prepared as described in Example 1b). mp=195°–197° C. The UV spectrum of Compound 1 (isopropanol solution) exhibits a λmax=336 (ε=44,920).

EXAMPLE 4

Synthesis of Compound 2

(a) Synthesis of 4-methoxycinnamoyl chloride

A 1000 mL round bottom flask equipped with a magnetic stir bar, reflux condenser, dropping funnel, and argon inlet is charged with 30.0 g (0.17 mol) of 4-methoxycinnamic acid and 500 ml of benzene. Next, 40.5 ml (66.1 g, 0.56 mol) of thionyl chloride is added dropwise. After the addition is complete, the reaction mixture is heated to reflux for five hours. Heating is discontinued and the mixture allowed to stir overnight. The benzene is removed by rotary evaporation to yield 33.6 g (0.17 mol, 100%) of a beige solid. Proton NMR and IR are consistent with the proposed structure. This material is used without further purification.

(b) Synthesis of Compound 2

A 50 mL, round-bottomed flask equipped with a magnetic stir bar and a reflux condenser is charged with 4-methoxycinnamoyl chloride (1.0 g, 5.0 mmol) and 25 mL and freshly distilled THF. This mixture then is chilled in an ice salt bath. Next, a solution of 4-hydroxydibenzoylmethane (1.0 g, 4.0 mmol; which is prepared as described in Example 1b) dissolved in a mixture of 3 mL dry pyridine and 5 mL THF is added dropwise to the reaction flask. The reaction mixture is then heated to reflux for 1 hour, after which time the reaction mixture is cooled and poured into a mixture of 20 g of ice and 3 mL conc. hydrochloric acid. The fine white solid which precipitates is collected by suction filtration; m.p.=149°–151° C. Analysis calcd. for $C_{25}H_{20}O_5$: C, 74.99; H, 5.03; O, 19.98. Found: C, 74.77; H, 5.03; O, 20.12. The UV spectrum of Compound 2 (isopropanol solution) exhibits a $\lambda max=338$ ($\epsilon=47,200$).

EXAMPLE 5

Synthesis of Compound 3

(a) Synthesis of 4-hydroxy-4'-methoxydibenzoylmethane

This compound is prepared by a procedure analogous to the procedure used to prepare 4-hydroxydibenzoylmethane, but using methyl 4-methoxybenzoate in place of the methyl benzoate as used in Example 1b. mp=180°–182° C. Anal. calcd for $C_{16}H_{14}O_4$: C, 71.10; H, 5.22; O, 23.68. Found: C, 71.15; H 5.54; O, 23.47.

(b) Synthesis of Compound 3

By a procedure essentially the same as that described in Example 4 hereinbefore, Compound 3 is synthesized from 4-methoxycinnamoyl chloride (which is prepared as described in Example 4a) and 4-hydroxy-4'-methoxydibenzoylmethane. The crude material is recrystallized from acetone to yield a light yellow solid; mp=147.5°–149° C. The UV spectrum of Compound 3 (isopropanol solution) exhibits a $\lambda max=351$ ($\epsilon=45,000$).

EXAMPLE 6

Synthesis of Compound 6

A 100 mL, round-bottomed flask equipped with a magnetic stir bar, a condenser and positive nitrogen is charged with N,N-di-(2-ethylhexyl)-4-aminobenzoic acid (5.0 g, 0.0138 mole, F.W. 361). To this is added 4-hydroxydi-benzoylmethane (3.32 g, 0.0138 mole, F.W. 240), followed by 30 mL of polyphosphate reagent (made by refluxing a mixture of, for example, 161 g (1.14 mole) of phosphorus pentoxide, 151 mL anhydrous ether and 322 mL of chloroform for 16 hours).

This solution is stirred magnetically and heated in an oil-bath for 16 hours, at 80° C.

This reaction mixture is then allowed to cool and 100 mL of anhydrous diethyl ether is added. The resulting two phases are separated. The ether layer is washed with 50 mL of saturated sodium bicarbonate and dried over anhydrous magnesium sulfate. This mixture is then filtered and roto-evaporated to yield 5.64 g of an orange oil. (Theory yield of title compound 8.04 g). TLC (70/30 hexane/acetone) indicates mostly product r.f. 0.75.

This material is further purified by the HPLC to give material which is pure by TLC and the H-NMR, C-13 NMR, IR and Mass Spectra are in agreement with this structure and purity. H-NMR; $DCCl_3/TMS$: 0.6–2.0(m), 3.3(d), 6.5–6.8(m), 7.1–7.6(m), 7.8–82(m). C-13 NMR; $DCCl_3/TMS$: 185.26, 164.88, 154.92, 152.21, 135.45, 132.40, 132.05, 128.66, 127.10, 122.21, 114.26, 93.01, 56.21, 36.86, 30.58, 28.68, 23.90, 23.15, 14.06, 10.71, IR salt plates: 2957m, 2912m, 2863m, 1715m, 1600s, 1520w, 1460w, 1271m, 1210m, 1180s, 1163s, 1060m, 1050m, 1015s, 1007s, 735s, 650m. Mass spectrum parent ion=583.

The UV spectrum of Compound 6 ($ClCH_2CH_2Cl$ solution) exhibits a $\lambda max=342.1$ nm ($\epsilon=31,000$).

EXAMPLE 7

Synthesis of Compound 7

The following reagents are placed into a 50 ml flask equipped with a magnetic stirrer and a drying tube:

N-(2-ethylhexyl)-N-methyl-4-aminobenzoate and 5.0 ml of polyphosphate ester (prepared by refluxing 204 g of phosphorous pentaoxide, 200 ml anhydrous diethyl ether and 425 ml of chloroform for 16 hours which results in a homogeneous solution). This mixture is then heated for 4 hours at 80° C. The homogeneous reaction solution is then allowed to cool and TLC (methylene chloride/methanol 99/1 on silica gel G) indicates most of the starting materials are gone and two new spots at larger r.f. values are present. This reaction solution is poured into 50 ml of methylene chloride and washed with 25 ml saturated sodium bicarbonate and 10 ml water. The resulting methylene chloride layer is then dried over magnesium sulfate. The mixture is filtered and the volatiles are removed by rotoevaporation to give 1.2 g of oil. The oil is then purified by HPLC to give two isomers. Mass spectral and NMR data confirm the structure of these compounds.

The UV spectrum of Compound 7 exhibits a $\lambda max=331.1$ nm ($\epsilon=26,480$).

EXAMPLES 8–14

The following sunscreen compositions are representative of the present invention:

| Component | Weight % Example # | | | | | | |
|---|---|---|---|---|---|---|---|
| | 8 | 9 | 10 | 11 | 12 | 13 | 14 |
| Sunscreen Compound: | | | | | | | |
| #(1) | 10 | — | — | — | — | 7.5 | — |
| #(2) | — | 3 | — | — | — | — | — |
| #(3) | — | — | 6 | — | — | — | 4.9 |
| #(4) | — | — | — | 10 | — | — | 2.1 |
| #(5) | — | — | — | — | 7.5 | 10 | — |
| Ethylene/Acrylate Copolymer[1] | 0.75 | 0.25 | 0.45 | 0.75 | 0.75 | 1.25 | 0.5 |
| Glycerin | 3.50 | 6.00 | 5.50 | 4.00 | 3.50 | 2.00 | 5.0 |
| Petrolatum | 1.50 | 2.50 | 2.00 | — | 1.50 | 0.50 | 2.0 |

-continued

| Component | 8 | 9 | 10 | 11 | 12 | 13 | 14 |
|---|---|---|---|---|---|---|---|
| Dimethicone[2] | 0.30 | 0.50 | 0.30 | 0.40 | 0.30 | 0.20 | 0.40 |
| Steareth-100 | 0.48 | 0.48 | 0.7 | 0.3 | 0.375 | 0.90 | 0.70 |
| Glycerol Monostearate | 0.32 | 0.32 | 0.8 | 0.7 | 0.875 | 0.80 | 0.30 |
| Cetyl Alcohol | 1.20 | 1.2 | 1.0 | 1.0 | 1.0 | 1.50 | 1.20 |
| Stearic Acid | 0.52 | 0.52 | 0.52 | 0.52 | 0.52 | 0.52 | 0.52 |
| Carbopol 934[3] | 0.08 | 0.08 | 0.15 | 0.09 | 0.18 | 0.20 | 0.10 |
| Carbopol 941[3] | 0.06 | 0.06 | 0.08 | 0.09 | 0.05 | 0.05 | 0.10 |
| Methyl Paraben[4] | 0.20 | 0.2 | 0.2 | 0.2 | 0.20 | 0.2 | 0.20 |
| Propyl Paraben | 0.10 | 0.1 | 0.1 | 0.1 | 0.10 | 0.1 | 0.10 |
| Imidazolidinyl Urea | 0.10 | 0.1 | 0.1 | 0.1 | 0.10 | 0.1 | 0.10 |
| Tetrasodium EDTA | 0.10 | 0.1 | 0.1 | 0.1 | 0.10 | 0.1 | 0.10 |
| Tyrosine | 0.10 | 0.1 | 0.1 | 0.1 | 0.10 | 0.1 | 0.10 |
| Potassium Hydroxide | 0.31 | 0.35 | 0.37 | 0.31 | 0.395 | 0.32 | 0.37 |
| Titanium Dioxide | 0.30 | 0.20 | 0.30 | 0.40 | 0.40 | 0.50 | 0.40 |
| Perfume | 0.18 | 0.08 | 0.15 | 0.13 | 0.10 | 0.25 | 0.15 |
| Water | 79.90 | 83.86 | 81.08 | 80.71 | 79.455 | 72.91 | 80.66 |
| TOTAL | 100.00 | 100.00 | 100.00 | 100.00 | 100.00 | 100.00 | 100.00 |

[1]Offered by Allied Chemical Company as AC 540A having a weight average molecular weight of 4271 and having 5% ethylene
[2]Polydimethylsiloxane offered by Dow Corning as DC-200
[3]Carboxyvinyl polymers offered by B. F. Goodrich
[4]Preservatives offered by Sutton Laboratories The above compositions can be made by adding the following components as described:

| Part | Material |
|---|---|
| I | Water |
| | Carbopol 934 |
| | Carbopol 941 |
| | Methyl Paraben |
| | Propyl Paraben |
| | Glycerin |
| II | Sunscreen Agents |
| | Cetyl Alcohol |
| | Glycerol Stearate |
| | Steareth-100 |
| | Stearic Acid |
| | Dimethicone |
| | Petrolatum |
| | Ethylene/Acrylate Copolymer |
| III | Tetrasodium EDTA |
| | Potassium Hydroxide |
| | Titanium Dioxide |
| IV | Tyrosine |
| | Imidazolidinyl Urea |
| | Perfume |

The composition is made by mixing the water phase (Part I) materials at 71°-99° C. in a scale-mounted mix tank fitted with baffles and an agitator. The oil phase (Part II) is mixed at 71°-110° C. in a separate mix tank fitted with an agitator. Both Part I and Part II are mixed until homogeneous phases are obtained.

The water phase (Part I) is then pumped into the oil phase (Part II) in an amount equal to 60–110% of the oil phase (Part II). This oil/water premix is held at a temperature of from about 71°-99° C. and agitated until a homogeneous mixture is obtained. The oil/water premix is then pumped into the remaining water phase (Part I) and held at a temperature of from about 71°-99° C. Part III ingredients are then added while maintaining agitation and holding the temperature at 71°-99° C. The composition is then passed through a closed vessel equipped with an ultrasonic probe at the flow rate of 0.5–6.5 kg/min. The ultrasonic frequency may range from 15 to 40 kHz. The composition is further processed through a heat exchanger and/or jacket cooling to a temperature of 71°-99° C. The part IV components are then added while maintaining agitation until a homogeneous mixture is obtained.

The composition is then pumped through a heat exchange to cool to 21°-32° C. While waiting to reach steady-state operation, the composition may be recirculated back to the mix tank. The composition is then packed into glass bottles.

The sunscreen composition of Example 11 is rubbed onto the skin of the person in need of protection from UVA and UVB wavelength radiation. A thin layer of this sunscreen composition is applied to the skin which will be exposed to the radiation. This sunscreen composition easy to apply to skin, and the sunscreen agent is not readily absorbed by the skin or readily rubbed off. Furthermore, it provides a constant and even protection against both UVA and UVB radiation.

EXAMPLE 15

Skin Penetration by Sunscreen Agents of the Present Invention

Skin penetration is done with human abdominal skin (Shriner's burns Institute) mounted on a ground-glass diffusion cell. The skin surface area exposed is 0.785 $cm^2$. The sunscreen agents are applied as a solution (100 microliters) in a vehicle (either ethanol or dimethyl isosorbide). The receiving reservoir is 4.5 ml of vehicle. The reservoir is stirred and maintained at 37° C. Penetration is determined by reading the UV absorbance of the reservoir. Assays are done in triplicate.

| Penetration of Sunscreen Agents of the Present Invention vs. Commonly Used Sunscreen Agents | |
|---|---|
| Sunscreen | Total Material Penetrated in 24 hrs. (ug/$cm^2$) |
| 2-ethylhexyl 4-N,N-dimethylaminobenzoate (ethanol vehicle) | 70 |
| 2-hydroxy-4-methoxybenzophenone (dimethyl isosorbide vehicle) | 21 |

-continued

| Penetration of Sunscreen Agents of the Present Invention vs. Commonly Used Sunscreen Agents | |
|---|---|
| Sunscreen | Total Material Penetrated in 24 hrs. (ug/cm$^2$) |
| Compound 4 (ethanol vehicle) | no penetration |

The low amount of skin penetration by the sunscreen agents useful in the present invention provides a uniform layer of protection for the skin against both UVA and UVB radiation. This protection against the UVA and UVB radiation will not vary with time as might occur by using a mixture containing molecules that are absorbed and/or rubbed off at different rates. Also, the relative UVA to UVB protection will not vary with time for the sunscreen agents of the present invention. Furthermore, the protection by the sunscreen agents of the present invention should last longer because it is less readily lost by absorption through the skin. Finally, there is less potential for toxicity (typically in the form of skin irritation) for the sunscreen agents of the present invention due to this low amount of skin penetration.

What is claimed is:

1. A sunscreen compound having the structure:

X—B—Z wherein
(a) —X is a UVA-absorbing moiety selected from the group consisting of those having the structures:

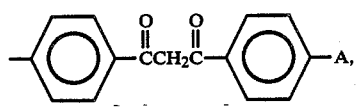
(i)

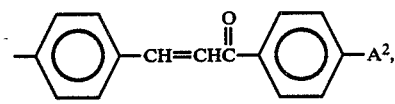
(ii)

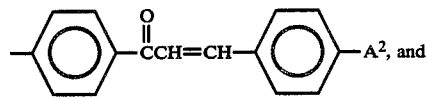
(iii)

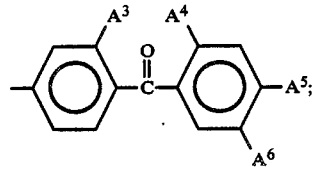
(iv)

(B) —Z is a UVB-absorbing moiety having the structure:

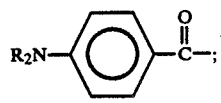

(c) —B— is a single bond or a linking group selected from —O— and —NR—;
wherein, in the above structures, —A is selected from the group consisting of —R, —OR, —NR$_2$ or —SO$_3$H, or its pharmaceutically-acceptable salt or ester; each —A$^2$ is independently —OR or —NR$_2$; —A$^3$ is —H or —OH; —A$^4$ and —A$^5$ are, independently, —R or —OR, and wherein further either —A$^3$ or —A$^4$ must be —OH; —A$^6$ is —H or —SO$_3$H, or its pharmaceutically-acceptable salt or ester; and each —R is independently —H, straight or branched chain alkyl having from about 1 to about 20 carbon atoms, —(CH$_2$CH$_2$O)$_m$H, or —(CH$_2$CH(CH$_3$)O)$_m$H, wherein m is an integer from 1 to about 8.

2. The sunscreen compound of claim 1 wherein —NR$_2$ is —NR$^1_2$, each —R$_1$ is independently straight or branched chain alkyl having from about 1 to about 20 carbon atoms, and —B— is selected from the group consisting of —O— and —NH—.

3. The sunscreen compound of claim 1 wherein —X has the structure:

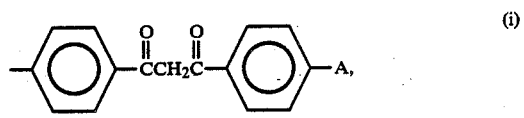
(i)

wherein —A is —R.

4. The sunscreen compound of claim 3 wherein —NR$_2$ is —NR$^1_2$, each —R$^1$ is independently straight or branched chain alkyl having from about 1 to about 20 carbon atoms, —B— is —O—, and —A is —H.

5. The sunscreen compound of claim 1 wherein —X has the structure:

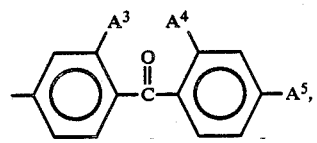

wherein —A$^5$ is —R, and either —A$^3$ or —A$^4$ is —H.

6. The sunscreen compound of claim 5 wherein —NR$_2$ is —NR$^1_2$, each —R$^1$ is independently straight or branched chain alkyl having from about 1 to about 20 carbon atoms, —B— is —O—, and —A$^5$ is —H.

7. A sunscreen compound according to claim 2 wherein —A$^2$ is selected from the group consisting of —OCH$_3$, —OCH$_2$CH$_3$, —OH and —NR$^1_2$; and each —NR$^1_2$ has one R$^1$ group being straight or branched alkyl having more than 2 carbon atoms and the other R$^1$ group is methyl or ethyl.

8. A sunscreen compound according to claim 4 wherein —NR$^1_2$ has one R$^1$ group being straight or branched alkyl having more than 2 carbon atoms and the other R$^1$ group is methyl or ethyl.

9. A sunscreen compound according to claim 6 wherein —NR$^1_2$ has one R$^1$ group being straight or branched alkyl having more than 2 carbon atoms and the other R$^1$ group is methyl or ethyl.

10. A sunscreen compound according to claim 1 selected from the group consisting of 4-N,N-dimethylaminobenzoic acid ester with 4-hydroxydibenzoylmethane; 4-N,N-(2-ethylhexyl)methylaminobenzoic acid ester with 4-hydroxydibenzoylmethane; 4-N,N-dimethylaminobenzoic acid ester with 2,4-dihydroxybenzophenone; N,N-di-(2-ethylhexyl)-4-aminobenzoic acid ester with 4-hydroxydibenzoyl methane; and 4-N,N-(2-ethylhexyl)methylaminobenzoic acid ester with 2,4-dihydroxybenzophenone.

11. A sunscreen compound of claim 10 selected from 4-N,N-(2-ethylhexyl)methylaminobenzoic acid ester with 4-(hydroxydibenzoylmethane and 4-N,N-(2-ethylhexyl)methylaminobenzoic acid ester with 2,4-dihydroxybenzophenone.

12. A sunscreen composition comprising:
(a) a sunscreen compound or mixture of compounds of claim 1; and
(b) a pharmaceutically-acceptable sunscreen carrier.

13. A sunscreen composition comprising:
(a) a sunscreen compound or mixture of compounds of claim 10; and
(b) a pharmaceutically-acceptable sunscreen carrier.

14. A sunscreen composition comprising:
(a) a sunscreen compound or mixture of compounds of claim 6; and
(b) a pharmaceutically-acceptable sunscreen carrier.

15. A method for protecting the skin of humans or lower animals from the effects of UVA and UVB wavelength radiation, said method comprising topically applying to the skin of the human or lower animal an effective coating of a sunscreen composition according to claim 12.

16. A method for protecting the skin of humans or lower animals from the effects of UVA and UVB wavelength radiation, said method comprising topically applying to the skin of the human or lower animal an effective coating of a sunscreen composition according to claim 13.

17. A method for protecting the skin of humans or lower animals from the effects of UVA and UVB wavelength radiation, said method comprising topically applying to the skin of the human or lower animal an effective coating of a sunscreen composition according to claim 14.

* * * * *

UNITED STATES PATENT AND TRADEMARK OFFICE
CERTIFICATE OF CORRECTION

PATENT NO. : 4,937,370
DATED : June 26, 1990
INVENTOR(S) : Anthony D. Sabatelli

It is certified that error appears in the above-identified patent and that said Letters Patent is hereby corrected as shown below:

Column 9, line 18, delete "$\alpha$max" and insert therefor --$\lambda$max--.

Column 21, line 12, delete "claim 10" and insert therefor --claim 4--.

Signed and Sealed this

Fourteenth Day of July, 1992

*Attest:*

DOUGLAS B. COMER

*Attesting Officer*   Acting Commissioner of Patents and Trademarks